(12) United States Patent
Lange

(10) Patent No.: US 11,164,674 B2
(45) Date of Patent: Nov. 2, 2021

(54) MULTIMODAL CRYPTOGRAPHIC DATA COMMUNICATIONS IN A REMOTE PATIENT MONITORING ENVIRONMENT

(71) Applicant: Medtronic, Inc., Minneapolis, MN (US)

(72) Inventor: Benjamin Lloyd Lange, Burnsville, MN (US)

(73) Assignee: MEDTRONIC, INC., Minneapolis, MN (US)

(*) Notice: Subject to any disclaimer, the term of this patent is extended or adjusted under 35 U.S.C. 154(b) by 0 days.

(21) Appl. No.: 16/752,200

(22) Filed: Jan. 24, 2020

(65) Prior Publication Data
US 2020/0162437 A1 May 21, 2020

Related U.S. Application Data

(62) Division of application No. 15/595,339, filed on May 15, 2017, now Pat. No. 10,554,632.

(51) Int. Cl.
H04L 9/32 (2006.01)
A61B 5/00 (2006.01)
(Continued)

(52) U.S. Cl.
CPC ............ G16H 40/67 (2018.01); A61B 5/0015 (2013.01); A61B 5/0022 (2013.01); H04L 9/3242 (2013.01); H04L 9/3247 (2013.01); H04L 63/0428 (2013.01); H04L 63/0435 (2013.01); H04L 63/123 (2013.01); H04L 63/18 (2013.01); H04W 12/069 (2021.01); H04W 12/106 (2021.01); H04L 2209/88 (2013.01)

(58) Field of Classification Search
CPC .. G16H 40/67; H04W 12/069; H04W 12/106; A61B 5/0022; A61B 5/0015; H04L 63/18; H04L 63/0428; H04L 63/0435; H04L 63/123; H04L 9/3247; H04L 9/3242; H04L 2209/88
See application file for complete search history.

(56) References Cited

U.S. PATENT DOCUMENTS 7,215,667 B1 * 5/2007 Davis ................. H04L 12/4633
370/389
10,554,632 B2 2/2020 Lange
(Continued)

OTHER PUBLICATIONS

Kent, S. IP Authentication Header. RFC 4302. Dec. 2005. (Year: 2005).*
(Continued)

Primary Examiner — Robert B Leung
(74) Attorney, Agent, or Firm — Shumaker & Sieffert, P.A.

(57) ABSTRACT

A system provides cryptographic means for securing the transmission of health data from devices of varying processing power and over various network protocols. The system is configured to transmit and receive packets to and from a remote patient monitoring device over multiple types of communication sessions. The system authenticates at least some of the data packet payloads and headers using multiple message authentication codes. The system can, for one type of communication session, the simulate or intercept acknowledgement packets generated for use with another type of communication session.

12 Claims, 7 Drawing Sheets

(51) Int. Cl.
*H04W 12/069* (2021.01)
*H04W 12/106* (2021.01)
*G16H 40/67* (2018.01)
*H04L 29/06* (2006.01)

(56) References Cited

U.S. PATENT DOCUMENTS

| | | | |
|---|---|---|---|
| 2001/0005883 A1* | 6/2001 | Wray | H04L 63/0823 713/151 |
| 2001/0002733 A1 | 10/2001 | Thompson | |
| 2001/0027331 A1 | 10/2001 | Thompson | |
| 2004/0193876 A1* | 9/2004 | Donley | H04L 63/1458 713/162 |
| 2005/0064846 A1 | 3/2005 | Karaoguz | |
| 2005/0210243 A1 | 9/2005 | Archard | |
| 2005/0283208 A1* | 12/2005 | Von Arx | A61N 1/37254 607/60 |
| 2006/0210071 A1 | 9/2006 | Chandran | |
| 2007/0061674 A1* | 3/2007 | Hansen | H04L 63/123 714/758 |
| 2008/0075079 A1* | 3/2008 | Smith | H04L 63/123 370/392 |
| 2011/0044454 A1* | 2/2011 | Baek | H04W 12/041 380/273 |
| 2011/0154453 A1 | 6/2011 | Hsu | |
| 2012/0233679 A1* | 9/2012 | Shedrinsky | H04W 12/068 726/7 |
| 2014/0368352 A1* | 12/2014 | Benjamin | A61B 5/7405 340/870.02 |
| 2016/0173364 A1 | 6/2016 | Pitio | |
| 2017/0126645 A1 | 5/2017 | Froelicher et al. | |

OTHER PUBLICATIONS

Kent, S. IP Encapsulating Security Payload (ESP). RFC 4303. Dec. 2005. (Year: 2005).*
Response to Examination Report from counterpart European Application No. 18731925.6 dated Oct. 2, 2020, filed Jan. 19, 2021, 14 pp.
Cprogramming.com, "Reading data from a socket", retrieved from https://faq.cprogramming.com/cgi-bin/, Feb. 12, 2005.
Security Requirements for Cryptographic Modules, Federal Information Processing Standards Publication, (Supercedes FIPS PUB 140-1, Jan. 11, 1994) Issued May 25, 2001, 61 pp.
Krawczyk, et al_ "HMAC: Keyed-Hashing for Message Authentication" RFC 2014 HMAC, retrieved Jun. 22, 2017, from https://ltools.ietf.org/html/rfc21 04, 12 pp.
Turning Data Into Actionable Insights, Software & Analytics, Medtronic, retrieved Jun. 22, 2017 from http:/lwww.medtronic.com/usen/healthcareprofessionals/services/caremanagementservices/poftwareanalytics.html, 3 pp.
International Search Report and Written Opinion, PCT/US2018/030557, dated Aug. 21, 2018, 16 pps.
Prosecution History from U.S. Pat. No. 10,554,632, dated Jan. 30, 2019 through Sep. 27, 2019, 21 pp.
Examination Report from counterpart European Application No. 18731925.6, dated Oct. 2, 2020, 4 pp.

* cited by examiner

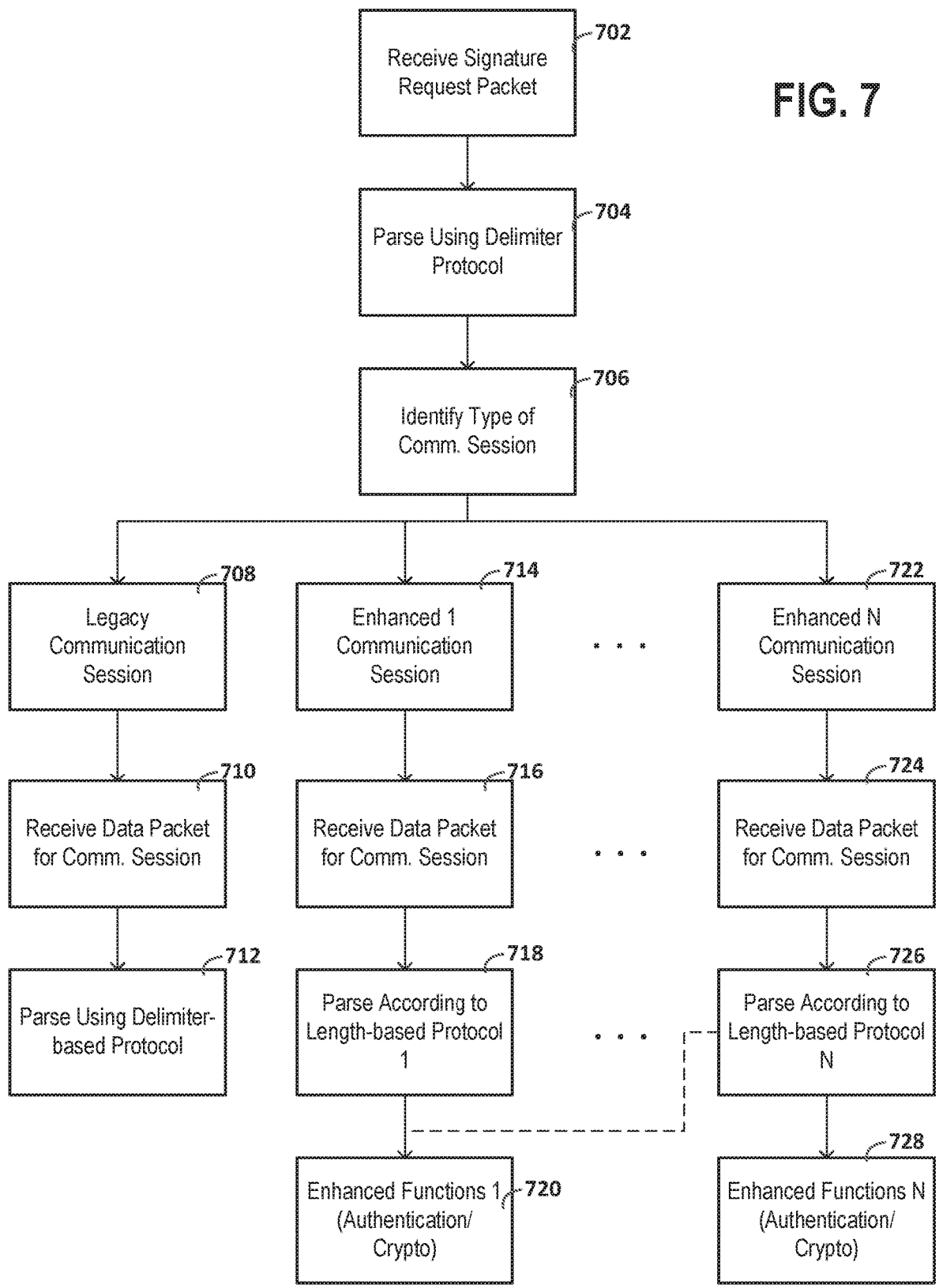

MULTIMODAL CRYPTOGRAPHIC DATA COMMUNICATIONS IN A REMOTE PATIENT MONITORING ENVIRONMENT

This application is a divisional of U.S. patent application Ser. No. 15/595,339, filed May 15, 2017, the entire content of which is incorporated herein by reference.

OVERVIEW

Remote patient monitoring is the practice of supervising a patient in a non-traditional location (e.g., the home) through remote patient monitoring devices (e.g., a glucometer, blood pressure monitor, or implantable device). The remote patient monitoring device measures a patient's physiological parameters and often transmits these measurements to a centralized repository. Remote patient monitoring is commonly used to manage chronic diseases (e.g., diabetes or heart failure).

SUMMARY

Various aspects of the present disclosure are directed to data security through cryptographic (or other) technologies used in conjunction with remote patient monitoring devices, systems, and uses, and in a manner that address challenges related to remote patient monitoring, including those discussed herein, and that are applicable to a variety of applications. These and other aspects of the present disclosure are described relative to multiple implementations and applications, some of which are shown in the figures and characterized in the claims section that follows.

Various embodiments are directed towards a system designed to enable secure transmission of health data from remote patient monitoring devices that have different encryption capabilities, which can be the result of differences in processing-power or use of different transmission networks and protocols.

Certain embodiments of the present disclosure are directed towards a remote patient monitoring system with a computer server. The computer server has a communication interface configured to receive, from remote patient monitoring devices, a plurality of signature request packets that include requests to initiate communication sessions. One or more processing circuits of the server are configured to parse content in the plurality of signature request packets according to a delimiter-based protocol that uses a start bit sequence an end bit sequence. The processing circuits can determine, based upon parsed content in a first signature request packet of the plurality of signature request packets, that a first communication session is an encrypted session. In response to the determination, the processing circuits identify an encryption key based upon the content in the first signature request packet and decrypt a portion of the first signature packet using the encryption key. The processing circuits create first session initiation data from the content in the first signature request packet and provide the first session initiation data to a legacy module. The processing circuits then receive a first data packet for the first communication session and parse content in the first data packet according to a length-based protocol that uses a length field to indicate the size of the first data packet. The processing circuits determine, based upon content in a second signature request packet of the plurality of signature request packets, that a second communication session is an unencrypted session. In response to the determination, the processing circuits provide, to the legacy module, the second signature request packet as second session initiation data. The processing circuit also receive a second data packet for the second communication session and parse content in the second data packet according to the delimiter-based protocol.

Certain embodiments of the present disclosure are directed towards a remote patient monitoring system that includes a computer server having one or more processing circuits configured to initiate, in response to a signature request packet from a remote patient monitoring device, an encrypted communication session. The processing circuits receive, from the remote patient monitoring device, a data packet for the initiated communication session and process, in response to the encrypted communication session, the data packet by: identifying transaction details from unencrypted data fields in a packet header; and verifying the authenticity of the data packet. The authenticity can be verified by authenticating the header content, including the unencrypted data fields and a payload message authentication code, against a header message authentication code; and authenticating payload content against the payload message authentication code. The processing circuits decrypt the payload and transmit, for the encrypted communication session and the unencrypted communication session, the payload to a patient data processing system.

Certain embodiments of the present disclosure are directed towards a remote patient monitoring system that includes a computer server having one or more processing circuits configured to receive signature request packets from a plurality of remote patient monitoring devices. The processing circuits determine, in response to an indication in the signature packets, whether each signature packet is for an encrypted communication session or unencrypted communication session and initiate, in response to the determinations, encrypted communication sessions and unencrypted communication sessions. The processing circuits receive, from the plurality of remote patient monitoring devices and for the communication sessions, incoming data packets that include a packet header and a payload. For the incoming data packets of encrypted communication sessions, the processing circuits: verify the incoming data packet content against a message authentication code; provide the verified incoming data packet content to a patient data processing system; and intercept, from the patient data processing system, genuine acknowledgement packets for the incoming packet content. For incoming data packets of unencrypted communication sessions, the processing circuits receive, from the patient data processing system, genuine acknowledgement packets for the incoming data packets; and transmit the genuine acknowledgement packets to corresponding remote patient monitoring devices of the plurality of remote patient monitoring devices.

The above summary is not intended to describe each illustrated embodiment or every implementation of the present disclosure.

BRIEF DESCRIPTION OF THE DRAWINGS

FIG. 7 is a flow diagram for handling multiple types of enhanced communication sessions, consistent with embodiments of the present disclosure.

DETAILED DESCRIPTION

Figure 1:
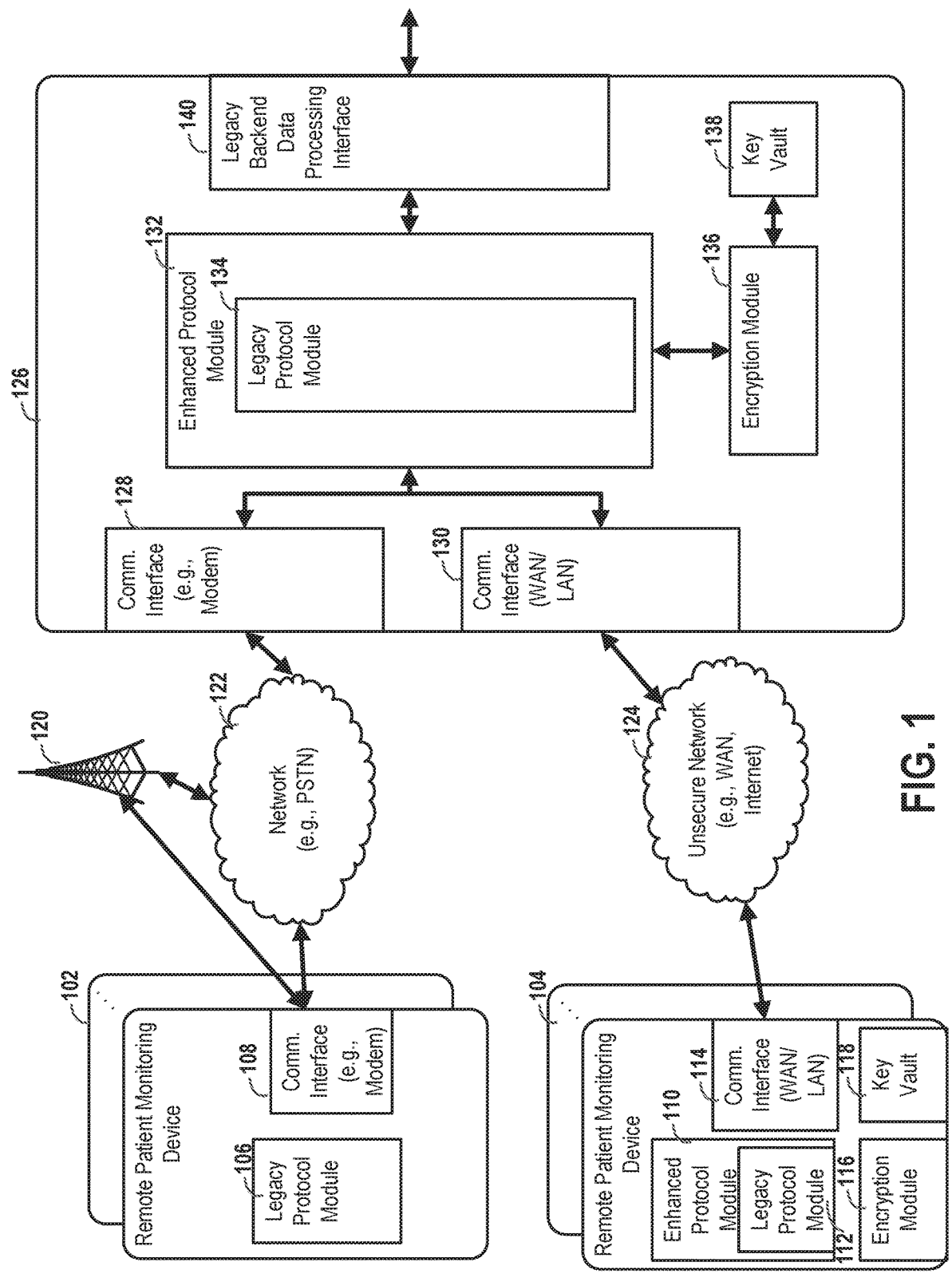
FIG. 1 illustrates a network containing legacy and non-legacy devices that can send data to a remote patient monitoring server, consistent with embodiments of the present disclosure.

Various aspects of the present disclosure relate to the transmission of patient health data from one or more remote patient monitoring devices to a computer server. More particular aspects relate to a computer server capable of securely receiving data using either an encrypted or unencrypted connections. While the present disclosure is not necessarily limited to such applications, various aspects of the invention may be appreciated through a discussion of various examples using this context.

The disclosure includes discussion of various embodiments, aspects, and features. Unless otherwise stated, the various embodiments, aspects, and features are contemplated as being used together in different combinations. For ease of discussion, and as a practical matter, each possible combination of features is not expressly recited. For example, the disclosure refers to aspects relating to different types of cryptographic hash functions (e.g., MD5 or SHA-256). It is understood that the system can have different combinations of these cryptographic hash functions, only one type of cryptographic hash function, or no cryptographic hash function at all.

Embodiments of the present disclosure are directed toward a remote patient monitoring server configured to collect and process data generated by one or more remote patient monitoring devices. The system may be configured to provide encryption, validation, and other security functions for data transmitted between the remote patient monitoring server and the remote patient monitoring devices. Embodiments of the system are configured to facilitate the use of preexisting remote patient monitoring devices ("legacy devices") simultaneously with new remote patient monitoring devices ("non-legacy devices") that may be configured to have different (expanded) capabilities relative to the capabilities of a legacy device. Moreover, certain implementations of the remote patient monitoring server may include an enhanced protocol module configured to support the expanded capabilities while also utilizing legacy data processing modules and protocols to provide support for legacy devices.

Aspects of the present disclosure relate to the recognition that the healthcare environment presents challenges to the replacement, upgrading, or updating of remote patient monitoring devices. While the various embodiments discussed herein are not necessarily limited by this or other such recognitions, the recognitions may help to facilitate discussion of various aspects. For example, patient familiarity with remote patient monitoring devices may cause healthcare providers to be reluctant to replace remote patient monitoring devices currently in use (e.g., legacy devices). The reluctance may be due, in part, to the resources necessary to provide new training for the patients as well as a fear of reduced patient participation due to a lack of patient familiarity with the new devices. Healthcare providers may have limited resources with which to educate a patient as to how to operate the patient's remote patient monitoring device or devices. It is also recognized that the software or hardware of a remote patient monitoring device may have limitations in its ability to be updated or upgraded. For instance, legacy devices may have limited computational or network resources (e.g., processing power, memory, or transmission capabilities), making it impractical to implement features that use such resources, such as certain types of security and encryption. In another example, a legacy device may be an implanted device, and upgrading the of the device might therefore be difficult and potentially introduce added risk to a patient. Accordingly, various embodiments of the present disclosure are directed toward a system configured to provide support for both legacy devices and non-legacy devices.

Various embodiments of the present disclosure are directed towards a system for providing an encrypted or unencrypted communication session between a remote patient monitoring device and a remote patient monitoring server. In certain embodiments, the remote patient monitoring server includes an interface capable of receiving, from a remote patient monitoring device, signature request packets requesting either an encrypted or unencrypted communication session. The remote patient monitoring server is configured to initiate the requested type of communication session. As discussed in more detail herein, the remote patient monitoring server can be configured to support encrypted communication sessions, and associated protocols, in a manner that emulates unencrypted communication sessions. In this manner, other (legacy) modules of the system may have little or no changes to accommodate (and may not even be aware of) non-legacy devices and their encrypted communication sessions.

According to embodiments, an unencrypted communication session can use a relative secure connection or network, which can provide a certain level of security for the transmitted data. For example, a dedicated connection over a relatively private network, such as a public switched telephone network ("PSTN"), can provide a certain level of security between a remote patient monitoring device and a server. In this way, an unencrypted communication session can be used to securely transmit sensitive data (e.g., protected health information) from a remote patient monitoring device to a remote patient monitoring server. Conversely, a public network, such as the Internet, tends to be less secure but can offer other advantages, such as ease of access, improved data integrity, and increased bandwidth. Non-legacy devices can take advantage of the benefits of using a public network while providing additional security through an encrypted communication session, where data packets are encrypted before being transmitted between a remote patient monitoring device and a remote patient monitoring server. There may be other reasons for providing additional security including, but not limited to, differences in the content of the patient data being transmitted and differences in the environments (e.g., government versus private healthcare providers).

Consistent with various embodiments, the remote patient monitoring devices, whether legacy or not, use signature request packets to initiate a communication session with a remote patient monitoring server. The signature request packet includes information on whether the communication session being requested is to be a legacy (unencrypted) or non-legacy (encrypted) session. The remote patient monitoring server can thereby determine the type of session from the signature request packet. Consistent with various implementations, the remote patient monitoring server can also perform authentication of the signature request packets. In some implementations, the type of authentication can be different between encrypted and unencrypted sessions. For example, an encrypted session could use a using keyed-hash message authentication code (HMAC), while an unencrypted session might not use authentication (e.g., relying upon the private network to provide implicit authentication). After a communication session is initiated by a remote patient monitoring server, a signature response packet may be transmitted from the remote patient monitoring server to the remote patient monitoring device.

It is recognized that the remote patient monitoring server can be configured to handle more than two types of communications sessions. For instance, different versions of the remote patient monitoring devices could be released over time. Each version could potentially use a different type of communication session (e.g., a different encryption algorithm or scheme, different data packet format). The remote patient monitoring server can be configured to identify which type of communication session is requested based upon the content of the signature request packets. For ease of discussion, various embodiments are discussed in terms of two types of communications session; however, the corresponding embodiments are not necessarily limited to only two types of communication sessions.

Consistent with some embodiments, a signature request packet requests an encrypted or unencrypted communication session based on content in the signature request packet or signature request packet header. The remote patient monitoring server can parse the content by identifying a start bit sequence and an end bit sequence, which provide delimitation of the packet. It has been recognized that such a delimiter protocol could be problematic if the end bit sequence unintentionally appeared in a binary portion of the packet (e.g., portions of the packet that are created using encryption or a hash function). Such an occurrence might wrongly signal the end of the header and lead to data being dropped or otherwise incorrectly processed. Various embodiments are directed toward mapping the binary portion of the header into a reversible set of binary values that do not use the end bit sequence. For example, characters for the hexadecimal representation of the binary data could be mapped to a character encoding standard, such as the American Standard Code for Information Interchange (ASCII). The binary values could also be mapped to a proprietarily developed encoding scheme where the delimiter bit sequences would not be reproduced in the binary data. It is recognized that mapping from a purely binary space to an encoding space with restricted values necessarily uses more bits to convey the same amount of information or data. With respect to this recognition, various aspects of the present disclosure are discussed in more detail herein.

The consistent use of a delimiter-based protocol can be particularly useful for simplifying the processing of the incoming signature request packets. The remote patient monitoring server can thereby determine the type of communication session being requested by identifying a start bit sequence and end bit sequence in the signature request packet header, and then evaluating a value or a set of values present in the signature request packet header (e.g., values in a packet field that identifies the protocol). Based on the value or set of values, the remote patient monitoring server determines the type of communication session being requested by the signature request packet. According to various embodiments, a remote patient monitoring server can include an enhanced protocol module that is configured to process communications in a manner that can accommodate communications from the non-legacy devices.

According to certain embodiments of the present disclosure, the remote patient monitoring server is configured to process the signature request packet according to a first type of packet protocol (e.g., delimited protocol). Depending on the type of communication session that is initiated, the remote patient monitoring server can continue to use the first type for additional packets or switch to a second, different type of packet protocol (e.g., a length-based protocol). It is recognized that the data bits used to specify the data packet length for a length-based protocol increase the overhead in conveying the same amount of information or data. With respect to this recognition, various aspects of the present disclosure are discussed in more detail herein.

According to various embodiments of the present disclosure, the remote patient monitoring server is configured to authenticate data received from a remote patient monitoring device. For instance, data for an encrypted communication session can be communicated using a protocol in which the data includes a header message authentication code and payload message authentication code that are contained within an encrypted portion of a data packet header. Consistent with some embodiments, the authenticity of a data packet can be verified by authenticating unencrypted data packet header content against the encrypted header message authentication code and decrypted payload content against the encrypted payload message authentication code. In response to both the data packet header content and being positively authenticated, the remote patient monitoring server can decrypt the payload content. For both encrypted or unencrypted communication sessions, the unencrypted payload is transmitted to a data processing system.

Consistent with some embodiments, the data packet header, or a portion of the data packet header, may be encrypted. The data packet header may contain a payload message authentication code and a header message authentication code. The payload message authentication code and header message authentication code may be used to authenticate the authenticity of the sender and confirm that transaction details (e.g., payload content or header content) have not been modified. This helps to ensure the data packet was transmitted from a remote patient monitoring device to the remote patient monitoring server securely. For instance, a payload message authentication code and a header message authentication code are generated by a remote patient monitoring device using an authentication key and then placed in a data packet header. The remote patient monitoring device may also populate the header with transaction details that can be unencrypted and payload content that can be encrypted using a (symmetric) encryption key. The authentication key and encryption key are collectively referred to as a key set. In some embodiments, the authentication key and the encryption key could be the same, identical symmetric key. Other embodiments use separate symmetric keys for each of the authentication key and the encryption key, thereby providing additional security (e.g., in the event that one of the keys is compromised). The remote patient monitoring device transmits the data packet to a remote patient monitoring server. The remote patient monitoring server uses the authentication key to authenticate the unencrypted payload content and unencrypted header content relative to the payload message authentication code and the header message authentication code, respectively.

In certain embodiments, the data packet header has a fixed length relative to the type of communication session. The fixed length and facilitate the parsing of the header separate from the receipt and parsing of the data payload. The enhanced protocol module can identify the header contents, including the message authentication codes, by looking at data within a set number of bits relative to the beginning of the packet. This can be particularly useful for protecting against denial of service attacks that might otherwise exploit the use of length based protocols (e.g., by generating invalid packets with long/maximum length).

Consistent with some embodiments, data packets can be used to transmit data after the communication session has been initiated. The format and processing of the data packets can vary from that of the signature request packets. For example, a data packet may contain an encrypted or unencrypted payload. In an unencrypted communication session, an unencrypted payload may be transmitted from a remote patient monitoring device to a remote patient monitoring server and verified using an acknowledgement and sequence number. In another example, a checksum may be used to verify the data packet has not been corrupted during transmission from a remote patient monitoring device to a remote patient monitoring server through an unencrypted communication session. Conversely, in an encrypted communication session, an encrypted payload may be transmitted from a remote patient monitoring device to a remote patient monitoring server. As previously discussed, an encrypted payload may be authenticated by a payload message authentication code.

Various embodiments of the present disclosure are directed towards emulating a legacy protocol while also implementing an enhanced protocol. For example, the emulation may include simulating acknowledgement/non-acknowledgement (Ack/NAK) packets that are no longer used with the enhanced protocol. For instance, the legacy protocol modules in both the remote patient monitoring devices and remote patient monitoring servers may not be aware of the capabilities and details of enhanced protocol, or even aware that the enhanced protocol exists. The legacy modules may therefore still generate and expect to receive these acknowledgement packets; however, their generation or transmission may no longer be necessary for enhanced communication sessions. As an example, the new process of encryption and transmission may include mechanisms that verify both the receipt and the integrity of the transmitted data. The transmission and receipt of acknowledgment packets consume additional bandwidth, processing power, and time. Moreover, as discussed herein, modification of the underlying legacy components may be undesirable or impractical. Accordingly, an enhanced protocol module may be configured to locally generate the Ack/NAK packets, while intercepting Ack/NAK packets that would otherwise be transmitted.

Consistent with embodiments, the remote patient monitoring server will generate simulated acknowledgement packets for outgoing data packets from the data processing system. These acknowledgement packets are then provided to the data processing system in order to emulate the functionality of a legacy remote patient monitoring device. For incoming data packets, the server will intercept acknowledgement packets generated by the data processing system. The interception includes preventing the acknowledgement packets from being transmitted to the remote patient monitoring device.

Consistent with some embodiments, the server operates in a pass-through mode for genuine acknowledgement packets when the communication session is a legacy (e.g., unencrypted) session. In a legacy communication session, genuine acknowledgement packets are transmitted from a remote patient monitoring device to a remote patient monitoring server, and the remote patient monitoring server provides the genuine acknowledgement packets to a data processing system.

Turning now to the figures, FIG. 1 illustrates a network containing legacy and non-legacy devices that may be configured to send data to a computer server (remote patient monitoring server 126). Remote patient monitoring server 126 may be configured to receive data, such as patient health data, from remote patient monitoring devices 102 and 104. For instance, remote patient monitoring devices 102 or 104 may be, but are not limited to, a glucometer, blood pressure cuff, or weight scale.

Consistent with various embodiments discussed herein, the remote patient monitoring devices can include both legacy and non-legacy devices. For example, legacy devices 102 can include a legacy protocol module 106. The legacy protocol module 106 may be configured to use unencrypted communication sessions and transmit data over relatively secured networks, such as network 122, which can be, for example, private networks. Non-legacy devices 104 can use enhanced (e.g., encrypted) communication sessions and transmit data over relatively unsecured networks 124, such as the global Internet or other public wide area network (WAN) or local area network (LAN). The relative security of different networks is but one example of a reason for different versions of devices and types of communication sessions. For example, technology advances may allow for increased processing power and communication bandwidth. These advances can lead to enhanced features with different requirements and constraints, which can lead to changes in the type of communication session. Various embodiments discussed herein can be useful for facilitating changes to the type of communication session. Other considerations can also drive a need for one or more additional types of communication sessions to be supported.

Although not expressly depicted, one or more of the remote patient monitoring devices can be configured to transmit over multiple different types of networks. For instance, the non-legacy devices 104 may contain multiple communication interfaces, including interfaces designed to communicate over network 122. To accommodate the different communication pathways, remote patient monitoring server 126 may be configured to include multiple interfaces for communicating with remote patient monitor devices 102 and 104. For example, communication interface 128 may be configured to include a modem interface designed to communicate over a point-to-point connection (e.g., a dial up connection over the PSTN). Also as an example, communication interface 130 could be configured to include a network interface controller (NIC) that serves to provide a connection to the Internet.

Consistent with some embodiments, the system is configured to use signature packet requests to initiate communication sessions between remote patient monitoring devices 102 and 104, and remote patient monitoring server 126. For enhanced communication sessions that use encryption, a key set may be used to encrypt, decrypt, and authenticate the signature request packet as well as subsequent data packets. The keys of the key set can be symmetric keys known to both the server and remote devices. For instance, a symmetric encryption key can be stored on both the server 126 and remote patient monitoring devices 102 and 104. In some implementations, multiple keys can be used during the encryption, decryption, and authentication process. For example, an authentication key may be used for the authentication (e.g., using HMAC) while an independent encryption key can be used for the encryption or decryption. For ease of discussion, various embodiments are discussed in the context of a single key or single key set for each remote device; however, these embodiments are not necessarily limited to only one key.

In certain embodiments, access to the key set is controlled by a discrete hardware security component (e.g., an integrated hardware security module) connected to the remote patient monitoring device or remote patient monitoring server. The hardware security component can be designed to prevent the symmetric keys from being communicated in an unencrypted form and may provide multiple, different authentication and encryption functions for the associated device. For instance, an encryption key set can be generated and then shared between the remote patient monitoring devices and server. This operation can be carried out in a secure environment (e.g., a manufacturing or production environment). The hardware security components can then be called upon to encrypt, decrypt, and authenticate data, such as data from signature request packets.

Consistent with certain embodiments, a communication session is initiated between the remote patient monitoring server 126 and the remote patient monitoring device 102, 104 by generating session initiation data from a signature request packet. The session initiation data can include information for establishing the communication session, such as the unique identity of the remote patient monitoring device and the version of any software running on the remote patient monitoring device. The data structure and format for the session initiation data can be the same for both encrypted and unencrypted communication sessions (e.g., a delimiter-based protocol with common data fields in the packet), thereby facilitating the use of legacy backend data processing modules and systems with little or no modifications to account for updated and enhanced remote patient monitoring devices. The generated session initiation data is provided to a data processing system, which can verify that the data is valid as well as the identity and status of the remote patient monitoring device.

In an example, enhanced protocol module 132 can provide unencrypted data, from either an encrypted or unencrypted session, to legacy protocol module 134, and legacy protocol module 134 generates the session initiation data. Remote patient monitoring server 126 can then generate a signature response packet according to the type of communication session before transmitting the signature response packet to a remote patient monitoring device.

According to certain embodiments, legacy protocol module 134 is configured to generate a signature response packet that indicates the status of the communication session to the remote patient monitoring device that sent the signature request packet. For an encrypted communication session, the enhanced protocol module 132 can encrypt (at least a portion of) the signature response packet while also adding authentication data (e.g., using HMAC) to the signature response packet. For an unencrypted communication session, the enhanced protocol module can effectively operate in a pass-through mode by transmitting the signature response packet without significant modification.

After a communication session has been initiated, enhanced protocol module 132 determines the type of communication session that an incoming packet was transmitted to remote patient monitoring server 126 (e.g., an encrypted or non-encrypted session). Consistent with certain embodiments, the determination is based on the type of communication session that is currently open and active. For instance, after remote patient monitoring server 126 receives a signature request packet requesting an unencrypted communication session and initiating the unencrypted communication session, enhanced protocol module 132 can enter a legacy (e.g., unencrypted) state. Future packets received for the same session are automatically determined to be for a legacy state.

According to embodiments, enhanced protocol module 132 operates as a wrapper or interstitial layer between legacy protocol module 134, and communication interface 128 and communication interface 130. Legacy protocol module 134 may be configured to process legacy incoming packets (e.g., signature request packet requesting unencrypted communication session) according to a legacy protocol. Enhanced protocol module 132 may be used as an interstitial layer to enable remote patient monitoring server 126 to process incoming packets from either legacy devices or non-legacy devices while providing additional functions (e.g., security and encryption) before passing the processed data to legacy protocol module 134. For instance, a data packet is received at interface 140 for transmission to remote patient monitoring device to remote patient monitoring server 126. Enhanced protocol module 132 determines the data packet to be for an unencrypted-legacy communication session and provides the data packet to legacy protocol module 134 without significant (or any) modification. If enhanced protocol module 132 determines the data packet to be encrypted-enhanced protocol module 132 process the data packet to provide additional security and related enhancements before passing the data packet to legacy protocol module 134. Enhanced protocol module 132 may also provide additional security function for outgoing packets by processing packets received from legacy protocol module 134 before the packet is transmitted from remote patient monitoring server 126 to a remote device.

According to some embodiments, encryption functions can be provided by a separate encryption module 136. The enhanced protocol module 132 can invoke the encryption module 136 during the decryption of incoming packets, which can be provided to the data processing system. The enhanced protocol module 132 can also invoke the encryption module 136 during the encryption of outgoing packets, which can then be transmitted from remote patient monitoring server 126 to a remote patient monitoring device (e.g., through unsecure network 124). In particular implementations, encryption module 136 may be configured to encrypt outgoing packets or decrypt incoming packets using a hash algorithm (e.g., SHA-256), although other encryption algorithms can also be used. Consistent with embodiments of the present disclosure, a key set can be stored in a hardware key vault 138. The same key set may also be stored within key vault 118 to accommodate symmetric encryption and symmetric validation.

Legacy backend data processing interface 140 can be configured to provide an interface for remote patient monitoring server 126 to interact with a data processing system. The data processing system may be a patient data processing system, which can include, but is not limited to, an electronic medical record keeping system, a healthcare or patient data analytics engine, a healthcare management system, or any combination thereof. According to certain embodiments, the data processing system can utilize acknowledgement packets that indicate the status for received or transmitted data. As discussed in more detail herein, certain aspects of the present disclosure relate to simulation of acknowledgement packets for encrypted communication sessions. Accordingly, legacy backend data processing interface 140 may be configured to communicate with a data processing system. The communicated data may include, but is not limited to, session initiation data, a decrypted payload, a simulated acknowledgment packet, a genuine acknowledgement packet, and combinations thereof. Moreover, legacy backend data processing interface 140 may be configured to present the data in a legacy (unencrypted) format that is expected by the data processing system, irrespective of the type of communication session established with a remote patient monitoring device.

As discussed herein, network 122 can include various private networks, such as a public switched telephone network ("PSTN") or a cellular network requiring relay tower 120. Such networks may allow for point-to-point, or dedicated, connections between remote patient monitoring devices and the remote patient monitoring server 126. To facilitate communication between a legacy device and network 122, a legacy device may include a communications interface 108 that includes circuitry (e.g., to support a modem) that is configured to communicate with remote patient monitoring server 126 through network 122. A non-legacy device may communicate with remote patient monitoring server 126 through unsecure network 124 and using encryption to provide additional security.

Communication interface 114 (e.g., a WAN/LAN interface) may include circuitry (e.g., a NIC) that is configured to facilitate communication between remote patient monitoring server 126 and remote patient monitoring devices through unsecure network 124. A few examples of unsecure network 124 include an intranet (e.g., LAN, WAN), the global Internet, a cloud (e.g., IAN), or other types of area network. Enhanced protocol module 110 may be configured to instruct encryption module 116 to encrypt a packet before its transmittance to remote patient monitoring server 126. Encryption module 116 may be further configured to access a key set (encryption key and authentication key) stored within key vault 118 to facilitate encryption or decryption of the packet.

Additionally, a non-legacy device may include a legacy protocol module 112 that supports receipt and transmission of unencrypted data through secure networks, such as network 122. For instance, remote patient monitoring device 104 includes both enhanced protocol module 110 and legacy protocol module 112. Legacy protocol module 112 may be configured to process incoming and outgoing packets transmitted through a secure network. For instance, legacy protocol module 112 may be configured to assemble a packet before the packet is transmitted to remote patient monitoring device 126 through unsecure network 124 and to receive and process an incoming packet from remote patient monitoring device 126 (e.g., signature response packet).

Figure 2:
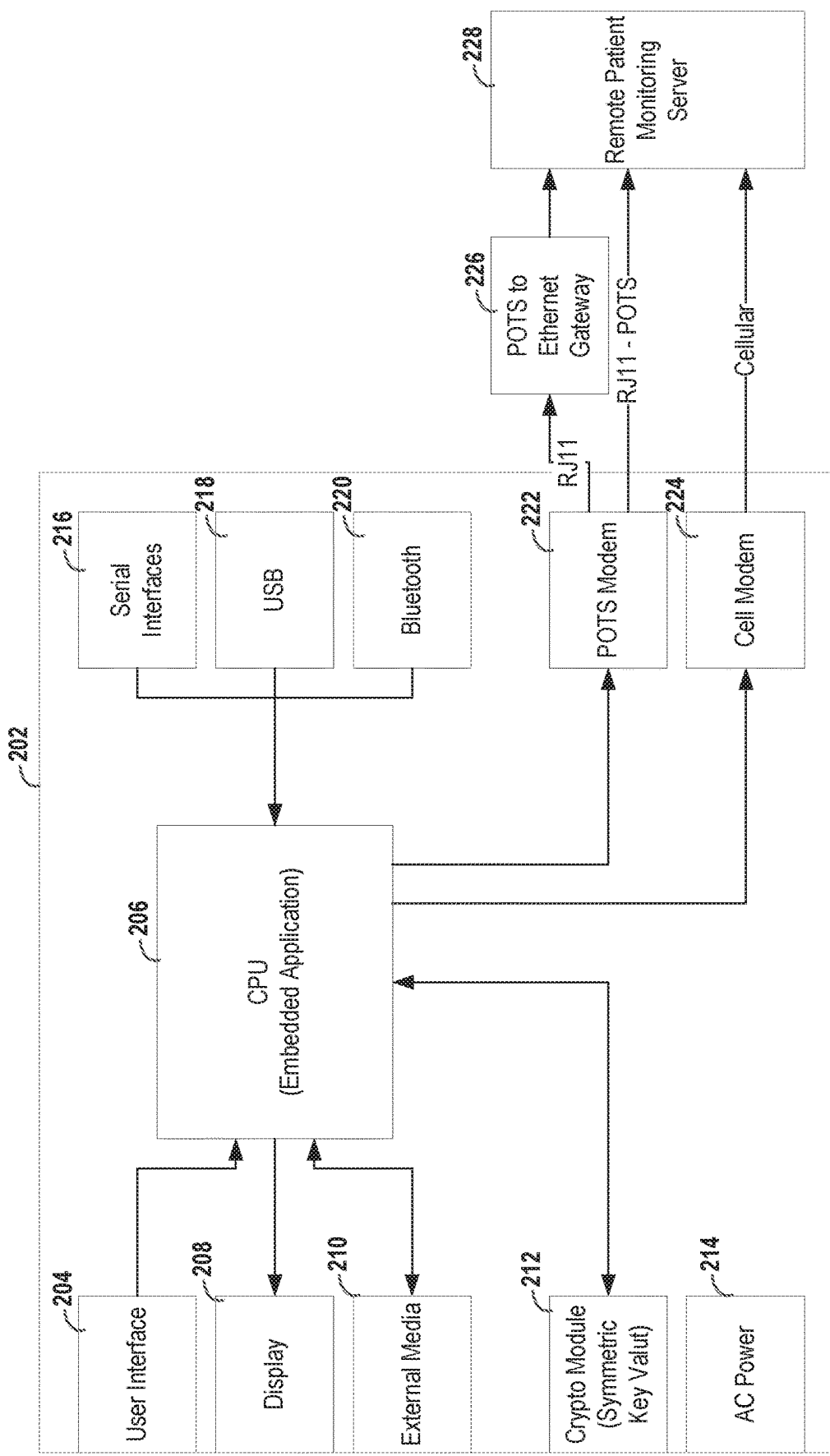
FIG. 2 illustrates a remote patient monitoring device in communication with a remote patient monitoring server, consistent with embodiments of the present disclosure.

FIG. 2 illustrates a remote patient monitoring device that is configured to communicate with a remote patient monitoring server, consistent with embodiments of the present disclosure. Remote patient monitoring device 202 can be consistent with the remote patient monitoring devices discussed in the context of various embodiments, including those discussed in connection with FIG. 1. For example, remote patient monitoring device 202 can collect patient health data and information, such as the patient's weight, blood pressure, or activity level. The remote patient monitoring device 202 can then initiate a communication session to transmit the patient information to remote patient monitoring server 228.

According to embodiments, the remote patient monitoring device 202 may be configured to receive data through one or more local communication interfaces 216, 218, and 220. The local interfaces can include, but are not limited to serial interface 216, USB interface 218, and Bluetooth interface 220. The local interfaces may be configured to enable communication between remote patient monitoring device 202 and other devices. For example, the patient monitoring device 202 can be configured to retrieve patient health data from measurement devices and sensors, such as from a weight scale or an implantable device. The monitoring device 202 can thereby operate as a centralized data collection node for the other devices and sensors. Data received through the local communication interfaces 216, 218, or 220 may be provided to central processing unit (CPU) 206 for processing and transmission.

The remote patient monitoring device may be configured to store instructions for an embedded application that can be executed by CPU 206. The embedded application can include one or more of the modules discussed herein, thereby providing control over communication of data with a remote patient monitoring server 228. If remote patient monitoring device 202 is a non-legacy device, remote patient monitoring device 202 may include an enhanced protocol module and may also include an encryption module and key vault, collectively represented by block 212. As previously discussed, the encryption module on a remote patient monitoring device may be configured to encrypt outgoing packets and decrypt incoming packets. The encryption module may be further configured to access a key set from the key vault to facilitate the encryption or decryption activity.

Remote patient monitoring device 202 may be configured to include one or more communication interfaces for transmitting packets to a server, such as remote patient monitoring server 228. For example, remote patient monitoring device 202 may be configured to include POTS modem 222 (e.g., RJ11 interface) and cell modem 224. These communication interfaces may each be configured to facilitate communication between remote patient monitoring device 202 and remote patient monitoring server 228 through a network (e.g., Internet, PSTN). In certain embodiments, POTS modem 222 may be further configured to communicate with remote patient monitoring server 228 through a gateway, such as POTS to Ethernet gateway 226. The specific examples of communication interfaces are provided as examples and are not meant to be limiting.

Remote patient monitoring device 202 may be further configured to include interfaces for facilitating human-computer interaction. In certain examples, remote patient monitoring device 202 may be configured to include user interface 204 and display 208. In certain embodiments, user interface 204 may be a keyboard or other type of hardware interface. and display 208 may be a LCD display or other type of display suitable for a remote patient monitoring device. For instance, a question regarding patient care compliance may be transmitted from remote patient monitoring server 228 to remote patient monitoring device 202. CPU 206 provides the question to display 208, and the user can provide an answer to the question through user interface 204. After an answer is provided, remote patient monitoring device 202 may be configured to transmit the user's answer to remote patient monitoring server 228.

Remote patient monitoring device 202 may be further configured to include an interface for connecting to external media (e.g., SD memory card). For instance, external media 210 may be configured to interface with a SD memory card and cause CPU 206 to update the firmware of remote patient monitoring device 202. In another example, external media 210 may be configured to interface with a USB flash drive and cause CPU 206 to transfer data received through serial interface 216, USB interface 218, or Bluetooth interface 220 to the USB flash drive.

Remote patient monitoring device 202 may be configured to receive power through a power interface, such as AC power 214. In particular, AC power 214 may be configured to accept power from an alternating current ("AC") socket.

Figure 3:
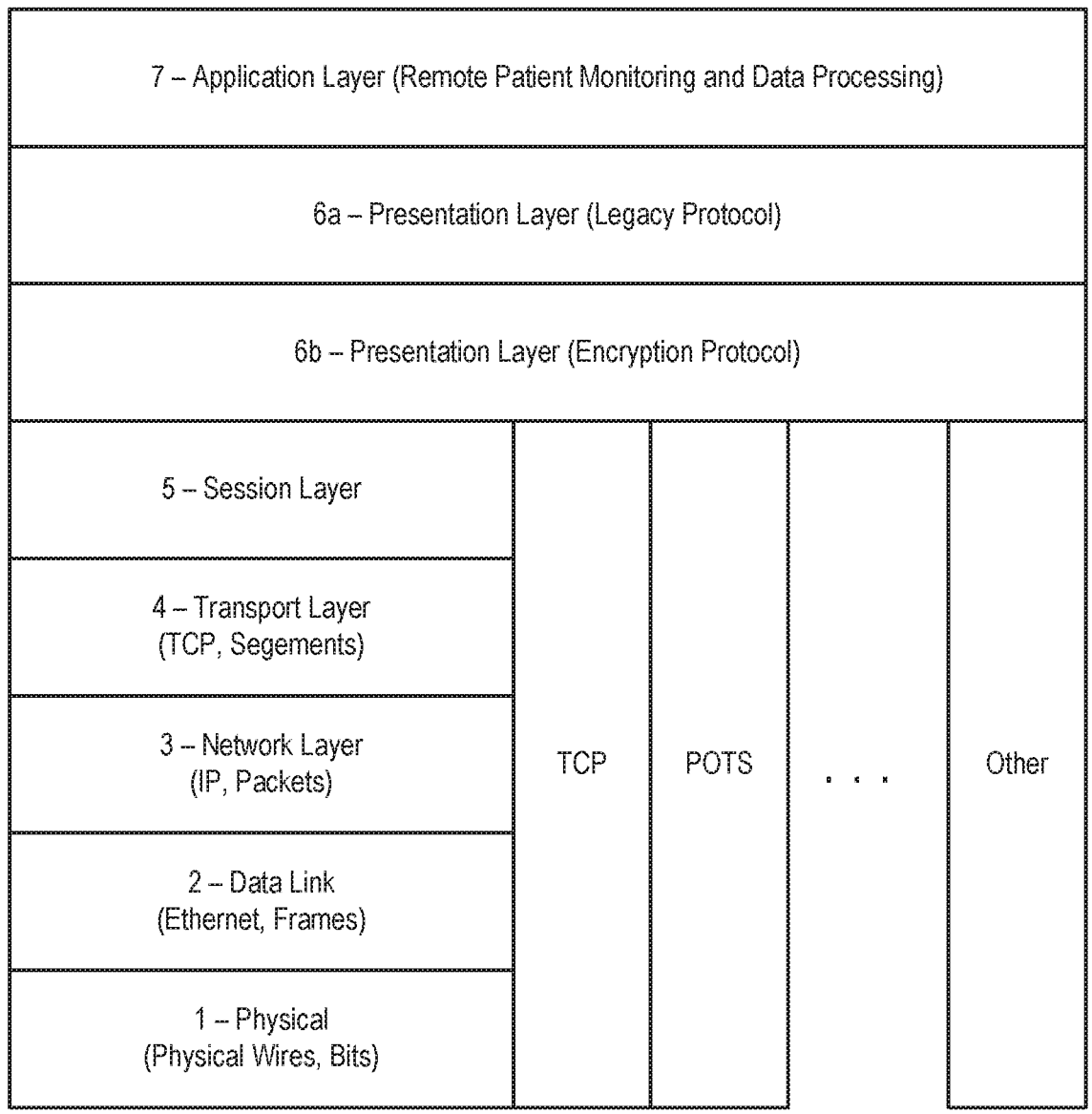
FIG. 3 illustrates the communication layers utilized by the system, consistent with embodiments of the present disclosure.

FIG. 3 illustrates the abstraction layers for a communication model utilized by a remote patient monitoring system, consistent with embodiments of the present disclosure. These abstraction layers relate to each other in a manner that is generally consistent with the open system interconnection model ("OSI model"). In the OSI model, the layers of a communication system are abstracted to demonstrate the relationship between components of a communication system beyond limitations related to underlying internal structure or technology. Each layer in the OSI model serves the layer above it and is served by the layer below it (e.g., the network layer serves the transport layer and is served by the data link layer).

Layer 6 is the presentation layer that establishes context between application-layer entities. Layer 6a is the layer that defines the packet-level format and processing for communication between a data processing system and a non-legacy remote patient monitoring device, such as remote patient monitoring device 102. For example, layer 6a can include the legacy protocol module that handles delimiter-based packets used by legacy remote patient monitoring devices. Layer 6b can function as an interstitial layer between layer 6a and layer 7. Layer 6b can provide additional functions relating to the communication between a data processing system and a legacy or non-legacy remote patient monitoring device, such as remote patient monitoring device 104. This configuration of abstraction layers can facilitate the expanding and updating of system capabilities without requiring significant changes to the remainder of the system. For example, by introducing a sublayer 6b, the functionality of the original/legacy layers 6a and 7 can be substantially unchanged, while adding non-legacy devices and maintaining support for communication with legacy devices. The sublayer 6b can provide enhanced features, such as encrypting, decrypting, and authentication, while outputting data that is otherwise consistent with the original 6a layer. Future enhancements can be handled by either modifying the sublayer 6b to handle of the additional features or by adding a new sublayer 6c. The ability to provide enhancements using such sublayers can be particularly useful for a remote patient monitoring system that supports many existing, legacy remote monitoring devices and has an established data processing and data analytics server or system.

For instance, an enhanced protocol module, such as enhanced protocol module 132, can be implemented at layer 6b, which is one level below what was the preexisting layer 6 (now layer 6a). The preexisting layer can correspond to legacy protocol module 134. As previously discussed, enhanced protocol module 132 may be configured to determine whether an incoming signature request packet is requesting an encrypted or unencrypted communication session. One aspect of the OSI model is the relative independent nature of each layer. In this context, the legacy protocol module operating at layer 6a may operate without knowledge of, or modification for, the enhanced protocol module at layer 6b. For instance, an enhanced protocol model can perform additional functions, such as encryption and authentication. At the same time, the data provided to and received from a legacy protocol module can match the format of similar data provided before the addition of the enhanced protocol module to the system. Moreover, certain implementations of the enhanced protocol module simulate messages between system components to account for differences in the enhanced functions. As discussed in more detail herein, the simulated messages can include acknowledgement messages otherwise used to confirm valid receipt of data.

Figure 4:
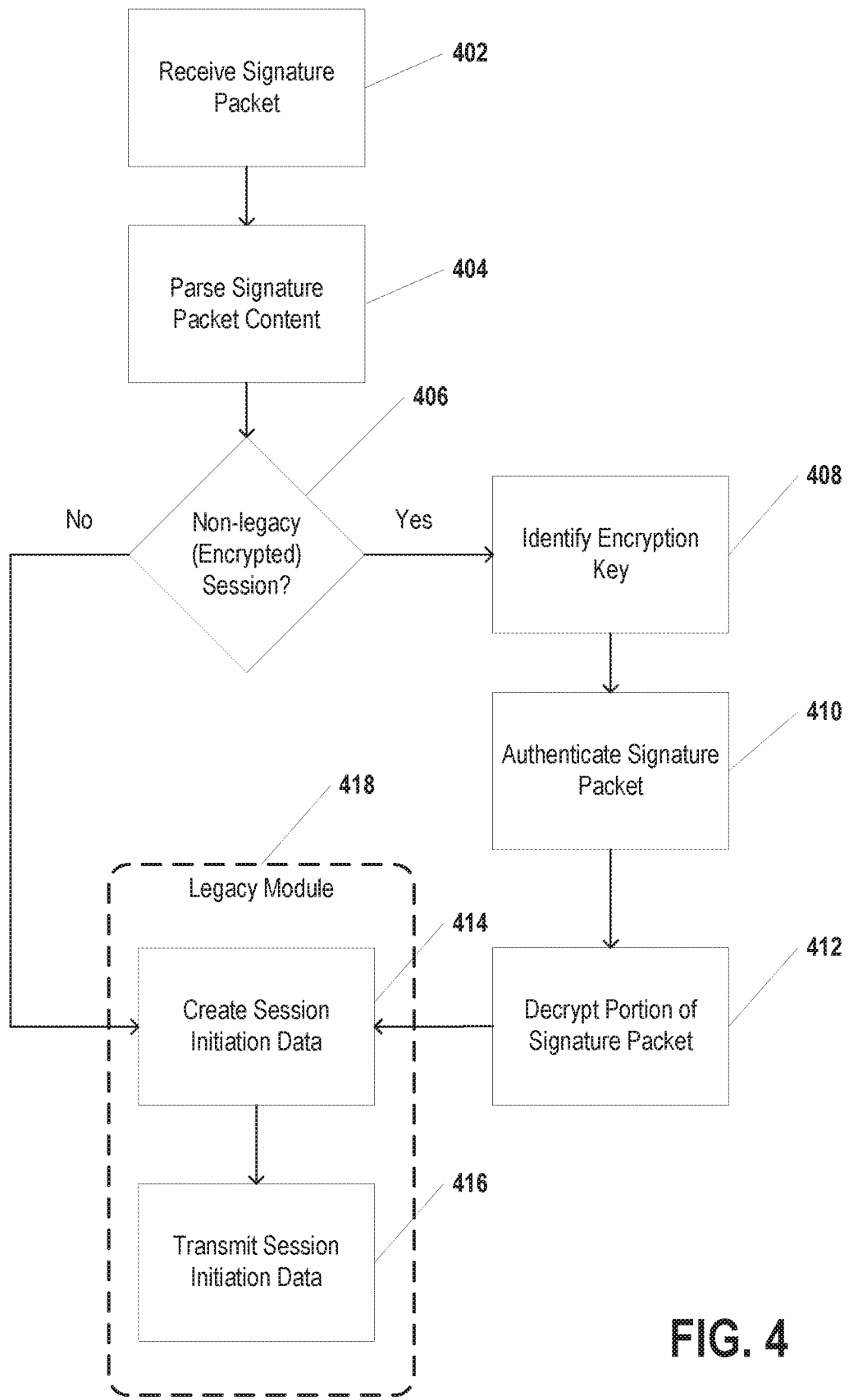
FIG. 4 is a flowchart demonstrating a method for receiving and processing a signature request packet, consistent with embodiments of the present disclosure.

FIG. 4 is a flowchart demonstrating a method for receiving and processing a signature request packet, consistent with embodiments of the present disclosure. At block 402, a remote patient monitoring server receives a signature request packet from a remote patient monitoring device.

After receiving a signature request packet, the signature request packet is provided by a communications interface, such as communication interface 128 or WAN interface 130, to an enhanced protocol module, such as enhanced protocol module 132. The enhanced protocol module then parses the unencrypted content of the signature request packet at block 404. The parsing can include identification of the start and end of the packet as identified by start and stop bit sequences.

Embodiments of the present disclosure are directed toward a signature request packet that can include encrypted and hashed portions for which the binary bits might inadvertently match the delimiter bit sequences. As such, the binary bits can be mapped into an encoding scheme in a manner that preserves the binary data while excluding the delimiter bit sequences from the set of valid bit sequences for representing the binary data. As but one example, the binary data could be mapped into a character encoding scheme, such as ASCII. For example, the binary value 1010 (the hexadecimal value of "A") and can be mapped to the ASCII binary value for the character "A," which is 1000001. Similarly, the binary value 0010 (the hexadecimal value of "2") can be mapped to the ASCII binary value for the character "2," which is 0110010.

Once the signature packet header has been parsed into its component parts, at block 406, the remote patient monitoring server can use the parsed data may to determine whether the signature request packet is requesting an enhanced or legacy communication session. As discussed herein, the enhanced communication session can use encryption and the legacy communication session can be unencrypted. For ease of discussion, FIG. 4 is discussed in the relative to encrypted or unencrypted communication sessions; however, the system can support communication sessions that have other differences (e.g., different types of encryption or different limitations on packet size).

As an example of how a communication session can be identified, the signature request packet may contain one or more fields that identify the type of communication session. The identification can be direct (e.g., a unique bit sequence for each type) or indirect (e.g., an identifier of the software version and device that the server can use to lookup to corresponding type). As previously discussed, a module within a remote patient monitoring server, such as an enhanced protocol module consistent with embodiments of the present disclosure, may be configured to carry out this determination. Certain embodiments are directed toward the use of a state machine, or similar solution, to control a communication session. The remote patient monitoring server can analyze the parsed data to determine whether the communication session is encrypted and then set the state machine into a corresponding mode or state. When future packets are received for the communication session, this state will implicitly indicate whether the communication session is an encrypted session.

If the enhanced module determines the signature request packet is not requesting an encrypted communication session, the enhanced protocol module provides the signature request packet to a module, such as the legacy module 418. In effect, the enhanced protocol module can operate in a pass-through mode where little or no modifications are made to the signature packet. At block 414, as previously discussed, legacy module 418 may be configured to create session initiation data based on the signature request packet. For instance, the legacy module 418 can format the data parsed from the signature request packet at block 404 into a form that is usable by a patient data processing system.

According to implementations, the contents of the signature request packet can vary depending on whether the signature request packet is for an unencrypted or an encrypted session. For example, a signature request packet for an encrypted communication session can contain a protocol version, an encryption key identifier, a client nonce, a data payload, and a hash value for authentication. In comparison, a signature request packet for an unencrypted communication session would not contain the encryption key identifier or the hash value. For example, a signature request packet for an unencrypted communication session can include information identifying the packet type, device identification, software version, and feature configuration information. In some implementations, portions of the signature request packet (for an encrypted session) can be encrypted while other portions are unencrypted. As an example, and with reference to the packet contents identified above, the encrypted portions of the signature request packet can include the data payload.

At block 416, the session initiation data is transmitted from the legacy module 418 to a data processing system, such as a patient data processing system.

At block 406, if the enhanced protocol module determines the signature request packet is requesting an encrypted communication session, the enhanced protocol module provides the signature request packet to an encryption module, such as encryption module 136. The encryption module, at step 408, identifies the encryption key, or key set, used by a remote patient monitoring device to encrypt at least a portion of the signature request packet. As discussed herein, identical copies of a key set can be stored on both the remote patient monitoring server and remote patient monitoring device to allow for symmetric encryption and authentication. In certain embodiments, the key set may be stored in discrete hardware security components (e.g., an integrated hardware security module) that are connected to the remote patient monitoring device or remote patient monitoring server. Accordingly, each remote patient monitoring device can have a unique key set, which can be identified based upon a corresponding unique device identifier contained within the signature request packet.

At block 410, an authentication key from the identified key set is used to authenticate the signature request packet. For example, the signature request packet can include an HMAC portion that can be used to verify that both devices have access to the same authentication key and that the data was not altered during transmission. Consistent with certain embodiments, the HMAC portion is generated relative to the entire packet (both the encrypted and unencrypted portions) to allow authentication of the entire signature request packet. The enhanced protocol module can further authenticate the identity of the remote patient monitoring device and whether the remote patient monitoring device is authorized to transmit data (e.g., by comparing a device identifier to a list of authorized devices). If enhanced protocol module 132 is unable to authenticate the identity of a remote patient monitoring device (e.g., the remote patient monitoring device is not recognized as being an authorized device within a remote patient monitoring network), enhanced protocol module 132 can reject the signature request packet and no communication session will be initiated.

At block 412, the enhanced protocol module can decrypt the encrypted portion of the signature request packet. In some embodiments, a key set is stored in a discrete hardware security module or device, such as key vault 138. The encryption module uses an encryption key from the key set to decrypt the encrypted portion of the signature request packet. The type of encryption being used can vary according to the desired level of security, the available processing power, and other considerations.

Assuming the signature request packet is affirmatively authenticated, data from the signature request packet, including the decrypted portion of the signature request packet, is provided to a legacy module, such as legacy module 418. As previously discussed, the legacy module may be configured to create session initiation data based on the provided data from the signature request packet. At block 416, the session initiation data is transmitted by legacy module 418 to a data processing system, such as a patient data processing system. The result of this process is the initiation of a communication session that allows for additional data packets to be communicated between the remote patient monitoring device and the remote patient monitoring server.

Figure 5:
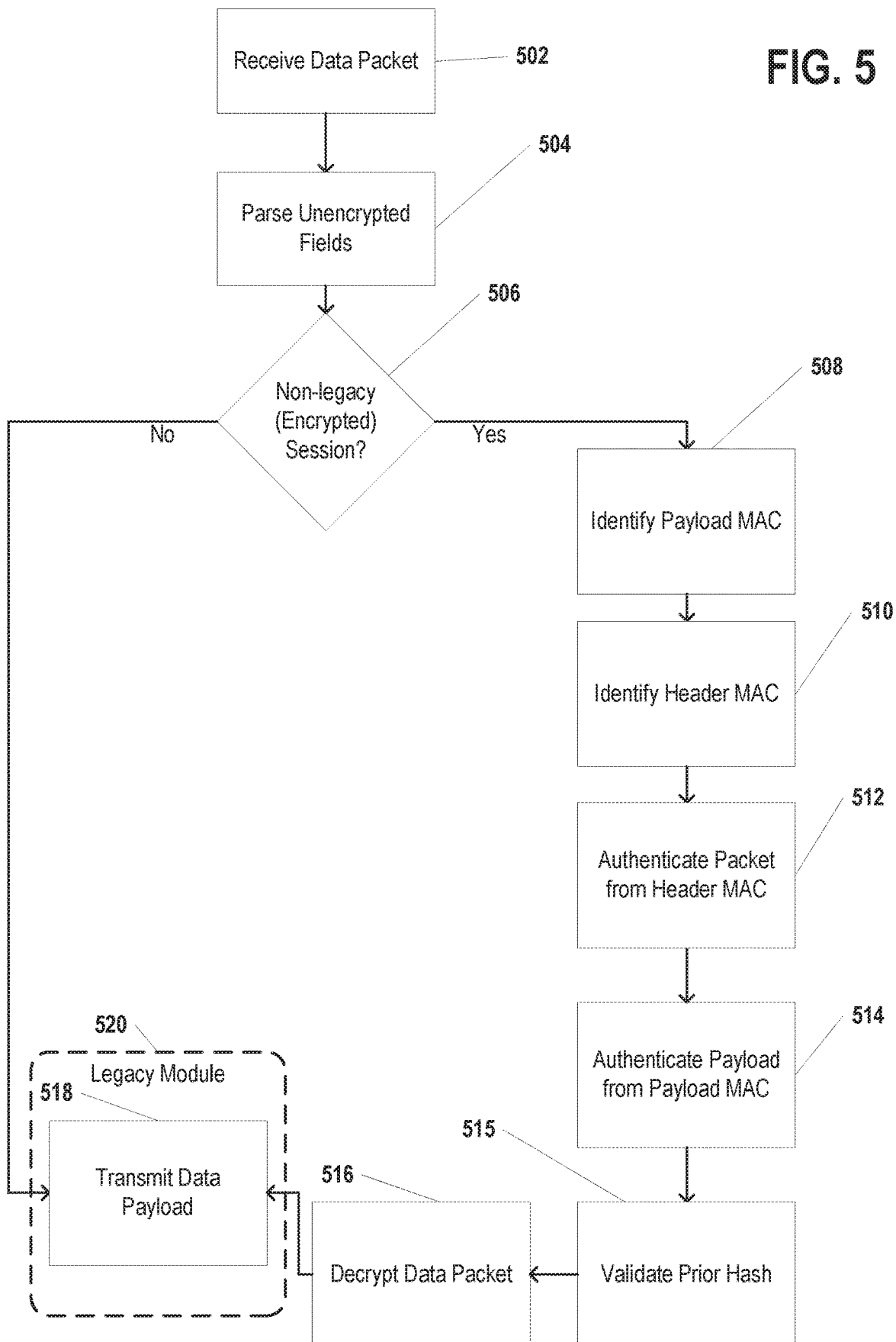
FIG. 5 is a flowchart demonstrating a method for receiving and processing an incoming data packet, consistent with embodiments of the present disclosure.

FIG. 5 is a flowchart demonstrating a method for receiving and processing an incoming data packet, consistent with embodiments of the present disclosure. The flowchart represents a situation where the communication session has already been initiated, such as through the process described in connection with FIG. 4. At block 502, a server, such as remote patient monitoring server 126 receives a data packet from a remote patient monitoring device, such as the remote patient monitoring devices discussed relative to FIG. 1 or other figures.

Consistent with some embodiments, a signature request packet for an encrypted communication session includes an encrypted portion and an unencrypted portion. The remote patient monitoring server can parse the unencrypted portion before decryption of the encrypted portion. As discussed herein, the unencrypted portion of the signature request packet can include data that can be used to authenticate the request packet, including authentication of both the unencrypted and the encrypted portion. Accordingly, the unencrypted portion can contain information that has less sensitivity in terms of content (e.g., a third party reading the data would not cause issues). For example, the unencrypted portion might include the data packet length/size, protocol version, key identifier, or other content and combinations of the content. The remote patient monitoring server can parse the unencrypted portion of the signature request packet. This parsed portion is then used to authenticate the signature request packet (e.g., using HMAC). The unencrypted portion of the signature request packet may include, but is not limited to, data relating to the device identity, type of message being transmitted, message identity, encryption protocol version, and a nonce value generated by the transmitting device.

According to embodiments, the remote patient monitoring server determines whether the received data packet is transmitted as part of legacy or non-legacy communication session, per block 506. For ease of discussion, the following description refers to embodiments in which the difference between a non-legacy and legacy communication session is the use of encryption. The determination of block 506 can be made based using various procedures. For example, the remote patient monitoring server can include state machine functionality for which the type of communication session of an open communication session is represented by a particular state, or set of states. The state can be set in response to receipt of a signature request packet (e.g., as discussed in FIG. 4). In this manner, the determination represented by block 506 is implicitly determined by the existing state. As another example, the remote patient monitoring server can store data identifying the type of session for all open communication sessions. The server can match a session identifier in the parsed data (e.g., a unique device identifier) to the stored data, which is then used to make the determination. In another example, each data packet can include one or more data fields the specify the communication type (e.g., by identifying the device or a software version).

If the enhanced protocol module determines the data packet was transmitted as part of an unencrypted communication session, the data packet is provided from the enhanced protocol module to a legacy module 520. Legacy module 520 can the process the data and provide the data to a data processing system, as shown by block 518. In this manner, the enhanced protocol module operates in a pass-through mode, allowing modules that are designed for use the legacy protocol to remain substantially unchanged in their function.

In some implementations, the remote patient monitoring device creates the data packet by first encrypting the data payload and generating the data MAC for this payload (e.g., a hash generated using HMAC). The data MAC is added to the packet header along with other information, such as the message index and message length fields. The header MAC is then generated for the header, which includes the data MAC. This nested use of MACs is then effectively reversed per blocks 508 through 516.

For instance, a payload message authentication code (MAC) and a header MAC are identified at blocks 508 and 510, respectively. According to various embodiments, the header MAC was generated so that it provides authentication for the entire message, including the data payload and payload MAC. Accordingly, the authentication of the header MAC, per block 512, provides confidence that the header content has not been altered or tampered with during transmission. The header content includes the payload MAC, which is therefore also verified—without first requiring the entire payload to have been received. In certain embodiments, the header can have a predetermined (or fixed) size so that the header can be authenticated once a set number of bits have been received. For instance, a HMAC authentication can be carried out once the set number of bits has been received.

As an example, the remote patient monitoring devices can generate a data packet with a predetermined or fixed header size and a payload with a size indicated by a length field within the header. The remote patient monitoring device can then rely upon the underlying layers, including the transport layer, to implement the transmission of the (application level) data packet to the remote patient monitoring server. For instance, a TCP/IP protocol could be used where the application level data packet is encapsulated in the TCP transport layer. The remote patient monitoring server can then retrieve the predetermined number of header bits from the TCP transport layer and uses the bits to authenticate the data packet at the application level.

It is recognized that the ability to verify header information independently from the payload can be useful for protection against denial of service attacks. For example, a denial of service attack might otherwise take advantage of the variable length of the data packet by generating a false data packet with header information indicating a long data length for the payload. Without a separate verification of the header, relative to the data payload, the server would continue to receive the entire payload before being able to verify the packet. The ability to separately verify the header allows the server to reject a data packet without needing to first wait for the entire payload to be delivered. This effectively decouples the time the server needs to reject a packet from the size of the payload (as indicated in the length field of the header). Moreover, using a predetermined size for the header can also prevent an attacker from generating long headers that require more time to receive and processes.

At block 514, the enhanced protocol module authenticates the data packet payload against the previously identified payload MAC using the symmetric authentication key. In response to the data packet header or headers being positively authenticated, the enhanced protocol module provides the data packet to an encryption module, such as encryption module 136.

According to various embodiments, the data packet header can contain information derived from a header MAC (e.g., a hash value) of a prior data packet. The use of a prior header MAC in this manner provides authentication between the consecutive chain of messages in the communication session. For instance, the generation of a valid data packet relies upon the knowledge about the contents of the prior packet(s). This presents yet another layer of protection from spoofing of other attacks. For instance, an attack might retransmit a prior valid packet as part of an attempt to overload the system. These packets could be quickly identified and ignored by checking the prior hash value. Accordingly, the enhanced protocol module can validate the prior MAC as shown in block 515.

At block 516, the encryption module decrypts the encrypted portion of the data packet, which includes the data payload. The encryption module then provides the decrypted data packet payload to the enhanced protocol module for further processing. After formatting the payload and header data, the decrypted data packet payload is then transmitted to a legacy module, such as legacy module 520, for additional processing. As previously discussed, the legacy module transmits the decrypted data packet payload to a data processing interface, such as legacy backend data processing interface 140, at step 518.

Figure 6:
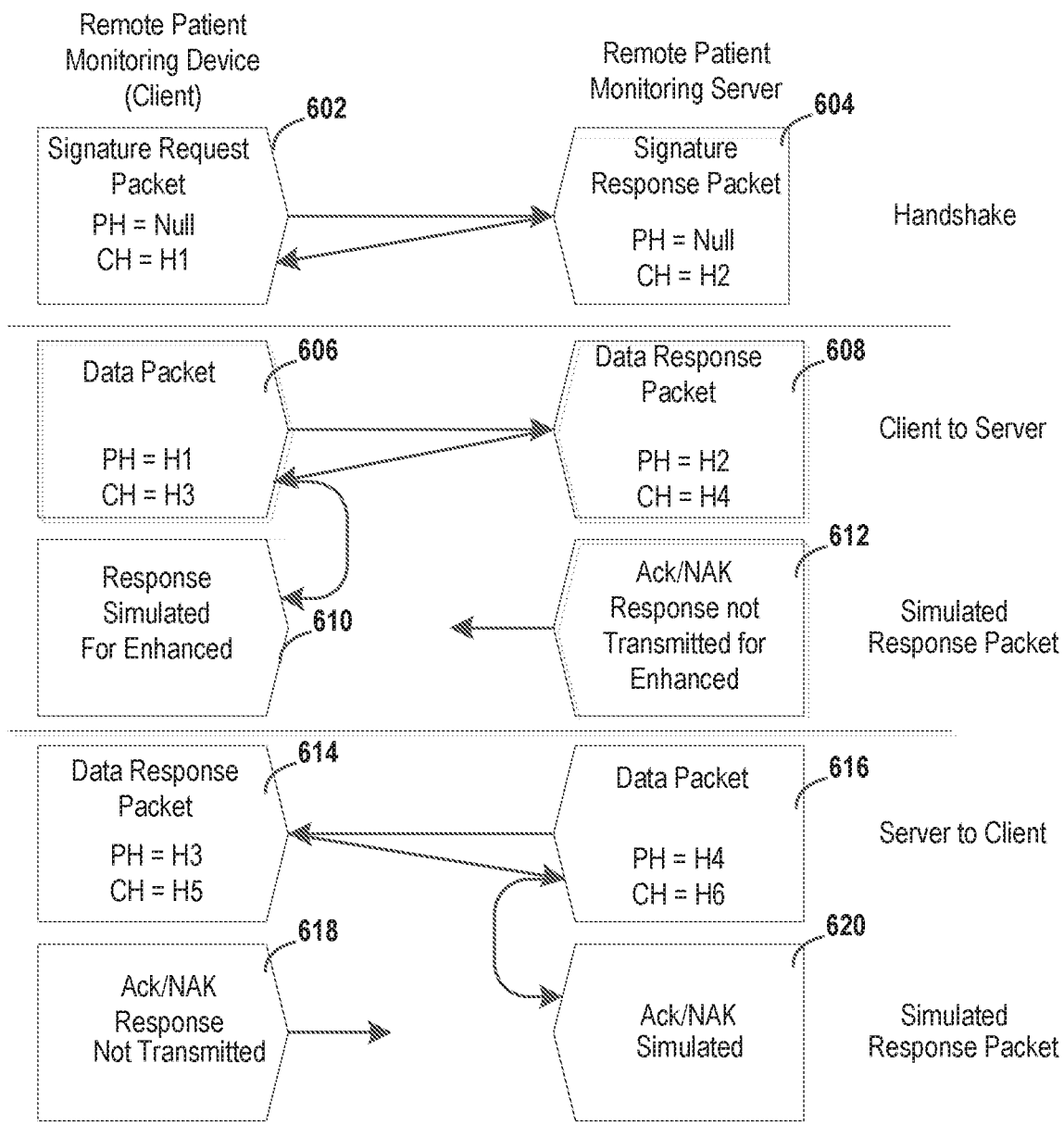
FIG. 6 is a flowchart demonstrating a method for simulating an acknowledgement packet, consistent with embodiments of the present disclosure.

FIG. 6 shows communication flow for acknowledgement packets, consistent with embodiments of the present disclosure. As discussed herein, the legacy system can be configured to use acknowledgement packets as part of the communication protocol. An acknowledgement packet may contain either a positive acknowledgment (Ack) or negative acknowledgement (NAK). The depicted blocks indicate the type of packet and contents. The arrows indicate the direction of the corresponding transmission (if any). Block 602 shows a signature request packet being transmitted from a remote patient monitoring device (client) to a remote patient monitoring server. The remote patient monitoring server responds with a signature response packet, per block 604. This initial exchange serves as a handshake that initiates the communication session.

After a communication session is initiated, the remote patient monitoring server can begin sending data packets to the remote patient monitoring server, as shown by block 606. The remote patient monitoring server can also respond with a data response packet, per block 608. Once the system has attempted to confirm the received data packet, the legacy module(s) of the system generate an appropriate Ack/NAK response packet, per block 612. The enhanced protocol module of the remote patient monitoring server receives the Ack/NAK responses and determines whether to transmit the response to the client or to intercept the response. For Ack/NAK response packets that are for an enhanced communication session, the enhanced protocol module intercepts the packets and prevents their transmission, as noted in block 612. Moreover, the remote patient monitoring device might also use legacy modules that generate and expect Ack/NAK messages. Accordingly, the remote patient monitoring device can generate a simulated Ack response packet (representing the intercepted packet), per block 610. For legacy communication sessions, the enhanced protocol module can operate as a pass through that allows the Ack/NAK messages to be transmitted. The Ack/NAK messages will therefore not be simulated.

For data packets originating from the server and intended for transmission to a remote patient monitoring device, per block 616, the process is effectively reversed. The client device can provide a data response packet, per block 614. Assuming the client device uses legacy modules that generate Ack/NAK responses, an enhanced protocol module of the client device can intercept the Ack/NAK response packet and prevent transmission, per block 618. The enhancement protocol module of the server can generate a simulated acknowledgement message, per block 620.

For an enhanced communication session, the remote patient monitoring server can allow the transmission of Ack/NAK response packets to a remote patient monitoring device in blocks 612 and 618. In this manner, genuine acknowledgement packets are received and used instead of simulating the packets as is otherwise shown in blocks 620 and 610.

Consistent with various embodiments of the present disclosure, the enhanced protocol module(s) can be configured to include a MAC (hash) value from prior data packets of the same communication session in the header of a current packet (e.g., as discussed in connection with FIG. 5). FIG. 6 shows an example of such a process by way of current hash (CH) and prior hash (PH) indicators. The numbers associated with the CH and PH represent consecutively generated MAC (hash) values. For example, the generation of the signature request packet, represented by block 602, is the first packet and the packet is generated by the remote patient monitoring device. Accordingly, the current hash is represented by value "1" and the prior hash value is "null" because there is no prior hash value.

According to various embodiments, the prior hash values are selected separately with respect to each of the remote patient monitoring device and remote patient monitoring server. For example, the generation of the signature response packet, per block 604, is the first packet generated by the remote patient monitoring server but the second packet in the session (the first packet having been generated by the remote patient monitoring device). Thus, the prior has value is set to "null" and the current hash value is represented by value "2." In this manner, the current hash always receives a new value because a new hash is generated for each packet. In subsequent packets, the remote patient monitoring server will include the hash from the prior packet generated by the remote patient monitoring server rather than the prior packet as received from the remote patient monitoring device. The remote patient monitoring device will follow a similar procedure, using the hash from the prior packet generated by the remote patient monitoring device rather than the remote patient monitoring server. This is represented by the respective current hash and prior hash values in the corresponding blocks of FIG. 6.

FIG. 7 is a flow diagram for handling multiple types of enhanced communication sessions, consistent with embodiments of the present disclosure. The flow beings with the receipt of a signature request packet a remote patient monitoring server, per block 702. The remote patient monitoring server can then parse the signature request packet, per block 704. In some embodiments, the legacy modules are configured to use a delimiter-based protocol that utilizes a delimiter-based protocol that uses a start and stop bit sequence to delimit the packet while facilitating the use of variable length signature request packets. One or more of the enhanced protocols can use binary data that can contain the start or stop bit sequences. For instance, some hash functions may map data into a binary data field of a fixed size where all bit values are potentially used. To avoid collisions with the delimiter values, binary for encrypted and hashed portions can be mapped into a set of values that do not contain the delimiter values.

According to an example implementation, the delimiter values for the signature request packet could be ASCII "start of text" and "end of text" values (00000010 and 0000011, respectively). The encrypted and hashed portions of a signature request packet could be mapped into the ASCII character values for the hexadecimal representation (characters 0 to F) of the binary values. The mapping for the binary data can vary and is not limited to a specific space or standard, so long as the mapped space does not result in collisions with the delimiter values and is reversible without the loss of data. Converting the binary in this manner can increase the number of bits used to convey the same amount of information as the original binary. Various embodiments are directed toward switching to a different protocol for enhanced communications sessions (e.g., a protocol that utilizes a packet length field).

The parsing of block 704 can identify the data contained within the data fields of the signature request packet. One or more of these data fields can include information that identifies the type of type of communication session (e.g., a device identifier or a software version code). Using the parsed data, the server can identify the type of communication session indicated by the signature request packet, per block 706. For instance, a corresponding communication session can be initiated, such as a legacy communication session (per block 708) or an enhanced (1) communication session (per block 714). Various embodiments are directed toward a system that is configured to use multiple (N) types of enhanced communication sessions, as shown by block 722.

According to certain embodiments of the present disclosure, received data packets (per blocks 708, 714, and 722), other than signature request packets, are correlated to the initiated communication session, for which the type of communication session has already been determined, as shown by block 706. Each data packet can then be parsed according to the corresponding protocol, per blocks 712, 718, and 726. According to various embodiments, one or more of the enhanced communication sessions can use a length-based protocol that defines the length of the packet using a length data field (e.g., as opposed to using delimiters), while the legacy communication sessions (and potentially one or more of the enhanced communication sessions) can use delimiter-based protocols to process subsequent data packets.

According to various embodiments, the length-based protocol can be used for communication sessions that have the capability of having large encrypted or hashed portions. For instance, the use of a length field represents a certain cost in additional bits, and the mapping of binary bits into a reduced space also represents a certain cost in additional bits. Further, each packet has an overhead cost in additional bits. These and other considerations can result in differing needs depending on the type of remote patient monitoring device and the capabilities thereof. As an example, remote patient monitoring devices that may generate large amounts of data for transmission at any given time might benefit from a length-based protocol that allows a large packet size and that does not require mapping of the binary data into a reduced space. In doing so, the relatively small size of the length field can be offset by the binary data size not being increased by mapping into a reduced space (e.g., as might otherwise be done to accommodate delimiters).

The remote patient monitoring server can also provide enhanced functions that are consistent with the corresponding type of communication session, as shown in blocks 720 and 728. According to some implementations, the enhanced functions can provide authentication (e.g., using HMAC) and cryptographic security; however, other types of functions can be provided as part of the enhanced functions (e.g., bit error detection or bit error correction).

According to various embodiments, the different types of communication sessions can share one or more functions. For instance, the dashed line between blocks 726 and 720 represents the possibility that the enhanced communication session N uses at least one function from the enhanced communication session 1. As a non-limiting example, the enhanced communication session N might use the same authentication (e.g., HMAC-based) protocol while using different cryptographic security (e.g., Data Encryption Standard versus Advanced Encryption Standard) protocols. Various other combinations of function sharing are possible.

According to embodiments of the present disclosure, a remote patient monitoring device can be configured to select between types of communication sessions that are available for use in the system. The selection may occur prior to the generation of the signature request packet. The remote patient monitoring device can indicate the selection in one or more fields of the signature request packet. The remote patient monitoring server can then identify the correct type of communication session from these fields.

For example, a remote patient monitoring device could select between different types of communications sessions based upon the amount of data to be transmitted. The different types can be tailored toward different amounts of data (e.g., relative to the maximum size of the data packet and the corresponding number of bits in the length field). As another example, a remote patient monitoring device could select between different types of communications sessions based upon the network being used or upon the type of data being transmitted. For instance, a first encryption and authentication solution could be used for transmission over a private network and a second (more secure) encryption and authentication solution could be used for transmission over a public network. Similarly, different types of encryption could be selected depending upon the content of the data (e.g., personal health data versus device status checks or firmware updates).

As used herein computer server (or just "server") is a device that includes hardware circuitry (e.g., one or more processing circuits or CPUs) that is configured to provide functions for other devices, which are sometimes referred to as clients of the server. For example, the remote patient monitoring devices can be clients of the remote patient monitoring server. The configuration of the hardware circuitry to provide functions for a computer server is possible through a variety of different solutions and implementations. For example, cloud solutions may offer virtual servers for which the underlying hardware circuits and resources may not be directly visible to the user of the cloud solutions. Such solutions, however, still operate by the configuration of the underlying hardware circuitry (e.g., in the form of one or more computer processors and associated memory circuits).

Various modules and circuits can be used to perform the operations and activities described herein. The modules include one or more circuits that are specifically designed to perform one or more of the operations and activities. The circuits can include discrete logic circuits or programmable logic circuits that, alone or in combination, are configured and arranged to implement the operations and activities. In certain instances, the modules include one or more computer processing circuits programmed to execute of stored instructions. The instructions can be in the form of firmware or software stored in a memory circuit that is accessible by the processing circuits. In addition, the various embodiments described herein may be combined in certain embodiments, and various aspects of individual embodiments may be implemented as separate embodiments.

Based upon the above discussion and illustrations, it is recognized that various modifications and changes may be made to the disclosed embodiments in a manner that does not require strictly adherence to the embodiments and applications illustrated and described herein. Such modifications do not depart from the true spirit and scope of various aspects of the disclosure, including aspects set forth in the claims.

The invention claimed is:

1. A remote patient monitoring system comprising:
    a computer server having one or more processing circuits configured to:
        initiate, in response to a first signature request packet from a first remote patient monitoring device, an encrypted communication session;
        receive, from the first remote patient monitoring device, a first data packet for the encrypted communication session;
        process, in response to receiving the first data packet for the encrypted communication session, the first data packet by:
            identifying transaction details from unencrypted data fields in a packet header of the first data packet; and
            verifying authenticity of the first data packet by:
                authenticating header content of the first data packet, including the unencrypted data fields and a payload message authentication code, against a header message authentication code; and
                authenticating payload content of the first data packet against the payload message authentication code; and
            decrypting the payload content of the first data packet;

transmit, for the encrypted communication session, the payload content of the first data packet to a patient data processing system;

initiate, in response to a second signature request packet from a second remote patient monitoring device, an unencrypted communication session;

receive, from the second remote patient monitoring device, a second data packet for the unencrypted communication session; and transmit, for the unencrypted communication session, payload content of the second data packet to the patient data processing system.

2. The system of claim 1, wherein the one or more processing circuits are further configured to identify transaction details from the unencrypted data fields in the packet header of the first data packet by retrieving a predetermined number of bits from a transport layer.

3. The system of claim 2, further comprising the first remote patient monitoring device, and wherein the first remote patient monitoring device is configured to generate the header message authentication code by applying a hash function to the packet header of the first data packet, the packet header of the first data packet including the predetermined number of bits.

4. The system of claim 1, wherein the one or more processing circuits are further configured to process the first signature request packet using a delimiter-based protocol.

5. The system of claim 4, wherein the one or more processing circuits are further configured to retrieve the payload content of the first data packet using a length-based protocol and information from a length field in the packet header of the first data packet.

6. The system of claim 1, wherein the one or more processing circuits are further configured to authenticate the header content of the first data packet using a first symmetric key and to decrypt the payload content of the first data packet using a second symmetric key that is different from the first symmetric key.

7. A remote patient monitoring system comprising:
a computer server having one or more processing circuits configured to:
receive signature request packets from a plurality of remote patient monitoring devices;
determine, in response to an indication in the signature request packets, whether each signature request packet is for an encrypted communication session or an unencrypted communication session;
initiate, in response to the determinations, encrypted communication sessions and unencrypted communication sessions;
receive, from the plurality of remote patient monitoring devices and for the encrypted communication sessions and the unencrypted communication sessions, incoming data packets that include a packet header and a payload;
for the incoming data packets of the encrypted communication sessions:
verify incoming data packet content of the incoming data packets of the encrypted communication sessions against message authentication codes of the packet headers of the incoming data packets of the encrypted communication sessions;
provide, to a patient data processing system, the verified incoming data packet content of the incoming data packets of the encrypted communication sessions; and
intercept, from the patient data processing system, genuine acknowledgement packets for the incoming data packets of the encrypted communication sessions; and
for the incoming data packets of the unencrypted communication sessions:
receive, from the patient data processing system, genuine acknowledgement packets for the incoming data packets of the unencrypted communication sessions; and
transmit, to first corresponding remote patient monitoring devices of the plurality of remote patient monitoring devices, the genuine acknowledgement packets for the incoming data packets of the unencrypted communication sessions.

8. The system of claim 7, wherein the one or more processing circuits are further configured to:
receive, from the patient data processing system, outgoing data packets of the encrypted communication sessions;
for the outgoing data packets of the encrypted communication sessions:
transmit the outgoing data packets of the encrypted communication sessions to second corresponding remote patient monitoring devices of the plurality of remote patient monitoring devices;
generate simulated acknowledgement packets for the outgoing data packets of the encrypted communication sessions; and
provide the simulated acknowledgement packets to the patient data processing system.

9. The system of claim 8, wherein the one or more processing circuits are further configured to:
for the outgoing data packets of the encrypted communication sessions:
encrypt at least a portion of the outgoing data packets of the encrypted communication sessions prior to transmitting the outgoing data packets of the encrypted communication sessions to the second corresponding remote patient monitoring devices; and
generate, for inclusion in the outgoing data packets of the encrypted communication sessions, the message authentication codes that provide confirmation that the output data packets of the encrypted communication sessions have not been modified during transmission.

10. The system of claim 7, further comprising the plurality of remote patient monitoring devices, wherein a specific remote patient monitoring device of the plurality of remote patient monitoring devices includes an enhanced protocol module configured to:
generate incoming data packets of a specific encrypted communication session of the encrypted communication sessions by:
encrypting at least a portion of the incoming data packets of the specific encrypted communication session, and
generating, for inclusion in the incoming data packets of the specific encrypted communication session, message authentication codes that provide confirmation that the incoming data packets of the specific encrypted communication session have not been modified during transmission;
generate simulated acknowledgement packets for outgoing data packets of the specific encrypted communication session; and provide the simulated acknowledgement packets to a legacy protocol module.

11. The system of claim 10, wherein the enhanced protocol module is further configured to receive the outgoing data packets of the specific encrypted communication session and intercept, from the legacy protocol module, genuine acknowledgement packets for the outgoing data packets of the specific encrypted communication session.

12. The system of claim 7, wherein the one or more processing circuits are further configured to:
receive, for outgoing data packets of the unencrypted communication sessions, genuine acknowledgement packets from the plurality of remote patient monitoring devices.

* * * * *